US008842267B2

(12) United States Patent
Heine et al.

(10) Patent No.: US 8,842,267 B2
(45) Date of Patent: Sep. 23, 2014

(54) DEVICE FOR DETERMINING PARTICLE SIZES

(75) Inventors: Martin Heine, Seuzach (CH); Stefan Manz, Constance (DE)

(73) Assignee: Bühler AG, Uzwil (CH)

( * ) Notice: Subject to any disclaimer, the term of this patent is extended or adjusted under 35 U.S.C. 154(b) by 59 days.

(21) Appl. No.: 13/509,465

(22) PCT Filed: Nov. 11, 2010

(86) PCT No.: PCT/EP2010/067274
§ 371 (c)(1),
(2), (4) Date: May 11, 2012

(87) PCT Pub. No.: WO2011/058092
PCT Pub. Date: May 19, 2011

(65) Prior Publication Data
US 2012/0224166 A1 Sep. 6, 2012

(30) Foreign Application Priority Data

Nov. 13, 2009 (EP) ..................................... 09175995

(51) Int. Cl.
*G01N 21/00* (2006.01)
*G01N 1/08* (2006.01)
*G01N 15/14* (2006.01)
*G01N 15/00* (2006.01)

(52) U.S. Cl.
CPC .......... *G01N 1/08* (2013.01); *G01N 2015/1472* (2013.01); *G01N 2015/0092* (2013.01); *G01N 15/1475* (2013.01); *G01N 15/147* (2013.01); *G01N 2015/0019* (2013.01)
USPC ........................................... 356/73; 356/335

(58) Field of Classification Search
CPC ........................ G01N 15/0205; G01N 15/1475
USPC ............... 356/73, 335–343, 600–622, 237.1; 340/962, 580, 583, 602; 250/574, 573, 250/575; 241/6, 33, 83; 382/110, 141
See application file for complete search history.

(56) References Cited

U.S. PATENT DOCUMENTS

| 3,949,614 A * | 4/1976 | Abonnenc .................. 73/863.83 |
| 2007/0205312 A1* | 9/2007 | Pierri et al. ...................... 241/6 |
| 2008/0218738 A1* | 9/2008 | Trainer ........................... 356/72 |

FOREIGN PATENT DOCUMENTS

| CA | 2417333 | 7/2004 |
| DE | 19510034 | 9/1996 |
| DE | 19802141 | 4/1999 |
| EP | 1464949 | 10/2004 |
| FR | 2258108 | 8/1975 |
| FR | 2421828 | 11/1979 |
| FR | 2628208 | 9/1989 |
| JP | 08-105866 A | 4/1996 |
| JP | 2000-146817 A | 5/2000 |
| JP | 20001-305040 A | 10/2001 |
| JP | 2002-061162 A | 2/2002 |
| JP | 2008-232466 A | 10/2008 |
| WO | 2006/116882 | 11/2006 |

* cited by examiner

*Primary Examiner* — Tri T Ton
(74) *Attorney, Agent, or Firm* — Shoemaker and Mattare (57) ABSTRACT

A method for measuring particle size distributions of bulk materials such as cereals, cereal milling products, cereal products and the like, which is intended to enable the measurement of particle size distributions which vary by orders of magnitude. A sample of isolated particles is optically detected in an arrangement by at least two measurement methods. Preferably, detection of the contours of the particles and laser diffraction take place at the same time.

22 Claims, 8 Drawing Sheets

DEVICE FOR DETERMINING PARTICLE SIZES

The invention relates to a method for measuring a size distribution of particles, in particular for optical online measurement of individual particles of bulk materials having wide particle-size distributions. The invention furthermore relates to a device for measuring particle-size distributions of this type.

The capture of particle sizes and the distribution thereof and also the determination of the content thereof using a specific measurement principle per se are known. For example, DE-C-19802141 discloses a device for determining the particle-size distribution by electro-optical scanning of a product stream using an optoelectronic measurement section. The image capturing apparatus described therein contains a plurality of electro-optical image recording appliances. Such a device is suitable for measuring particles having particle sizes of more than 100 µm. A disadvantage of this device and of the measurement method is that the measurement complexity and/or measurement errors increase greatly with decreasing particle size in particular for smaller particles having particle sizes of less than 100 µm. The reasons for this can be for example lack of optical resolution, optically distorted particle contours, lack of depth of field, disturbances owing to light diffraction or light scattering effects and/or motion blur.

Also known are devices for capturing particles by laser diffraction or laser scattering. Thereby it is possible to efficiently capture small particles having particle sizes ranging from about 1 µm to about 100 µm. However, the high complexity for the simultaneous capturing of larger particles, in particular having particle sizes of more than 1 mm, the lower measurement accuracy in this range, in particular for particles that deviate greatly from the spherical shape, and the low information content of the measurement method are disadvantageous. In particular, it is possible for only the projection-surface-area-based particle-size distribution and in part the particle concentration to be measured. Information relating to the detailed contours of the particles, as are determined during the image processing, is missing. Color, velocity or other particle properties likewise cannot be ascertained using laser diffraction.

According to the prior art, measurement values are captured using only one measurement principle, which limits the range of application and/or requires great complexity.

The invention is therefore based on the object of developing a method for determining a size distribution of particles, in particular for optically measuring particle-size distributions, which method avoids the disadvantages of the prior art and permits in particular online measurement, which is integrated in the bulk-material processing, of particle-size distributions ranging over several orders of magnitude.

This object is achieved by a method for determining a size distribution of particles, which contains at least the following steps:
a) producing a particle-containing product stream using a production method or providing a particle-containing product stream which was produced using a production method,
b) generating measurement data by capturing at least a portion of the particles, the measurement data being generated at least by optically capturing the portion of the particles using at least two different optical measurement methods,
c) determining at least one property of the portion of the particles on the basis of the measurement data which is captured optically in step b), at least one property being the size distribution of the portion of the particles.

The production method is selected from the group consisting of size-reduction, purifying, separation, mixing and agglomeration methods or any desired combinations thereof. The size-reduction method can be, for example, a milling method.

According to the invention, at least one optical measurement method comprises the capturing of a diffraction pattern of the portion of the particles.

Simultaneous capturing using at least two different optical measurement methods permits measurement of a larger range of particle sizes than would be possible using only one optical measurement method. For example, the method according to the invention can be used to capture for example particle-size distributions over a range of up to four orders of magnitude of particle. By way of example, particle sizes ranging from 2 µm to 20 mm can be captured, preferably ranging from 5 µm to 5 mm. In particular, the capturing of a diffraction pattern according to the invention permits measurement of particularly small particle sizes. This results in an improved ability to draw conclusions relating to the particle sizes and to their distribution in the product stream. This in turn permits a targeted adaptation of the production and processing parameters of particle-containing bulk materials, in particular of cereal milling products.

Measurement is carried out with preference online. Online means here and in the following text that the measurement is integrated in a process. In particular, measurement is carried out in terms of space in the immediate vicinity of the process.

The method can, for example, be used in the following areas:
processing of cereal, cereal grinding products and cereal end products of the milling facility (in particular grinding of common wheat, durum, rye, corn and/or barley) or special milling facility (in particular hulling and/or grinding of soy, buckwheat, barley, spelt, millet/sorghum, pseudo-cereals and/or pulses);
production of feedstuff for farmed or domestic animals, fish and crustaceans;
processing of oilseeds;
processing of biomass and production of energy pellets;
industrial malting and crushing plants;
processing of cocoa beans, nuts and coffee beans;
production of building materials;
production of fertilizers;
pharmaceutical industry;
solid-state chemistry.

With preference, a particle-containing sample is taken from the product stream produced or provided in step a), wherein in step b) the particles in this sample are optically captured. In this embodiment, the particles thus do not have to be measured in the product stream. Instead, the actual measurement can take place in step b) on the sample taken, which can extremely simplify the spatial arrangement of measurement apparatuses carrying out the measurement methods.

In possible embodiments, a sample can be taken in a down-pipe, for example using a screw shell. Sampling can be pulsed with respect to time. The proportion of the sample with respect to the entire product stream can be between 0.01% and 10%. As a result, a representative partial stream can be fed approximately continuously into the measurement without any further intermediate storage means.

In some embodiments, the sample can be metered, singulated and/or dispersed before the actual measurement in step b) takes place. Metering ensures that the correct quantity of product is fed to the measurement apparatuses with as little pulsation as possible. When singulating and dispersing, for example using the Venturi principle, however, the product stream can in some cases no longer be subjected to closed-loop control. In this case, the product can be diluted using pressurized air and further air which is taken from the environment by suction, so that all particles are present individually and can thus also be detected individually. This second step can be optimized separately from the metering in order to be able to singulate the product to various extents depending on its nature (e.g. strength of the interparticle adhesion forces). Transition from singulation to size reduction is fluent. Singulation and dispersion can in some cases be considered to be an inseparable step.

In preferred embodiments, at least one of the measurement methods in step b) comprises the capturing of projection surface areas of the portion of the particles. The particle contours of these projection surface areas can in that case be processed using particle contour processing.

The size distribution of at least one coarse fraction of the portion of the particles is preferably determined using particle contour processing, in particular in a size range from 10 µm to 30 000 µm, preferably from 50 µm to 20 000 µm, particularly preferably from 90 µm to 10 000 µm.

The size distribution of at least one fine fraction of the portion of the particles is determined likewise with preference using laser diffraction, in particular in a size range from 0.1 µm to 300 µm, preferably from 1 µm to 300 µm, particularly preferably from 5 µm to 200 µm.

In some embodiments, the optically captured measurement data can be used to determine, in addition to the size distribution of the portion of the particles, the form, the form factor, the color, a color component and/or the velocity of the portion of the particles. A form factor reduces a particle contour with any desired degree of complexity to a value. A form factor can for example be a measure of the "roundness" of a particle and could be defined as the quotient of the diameters of the equal-area and the equal-circumference circle. Typical form factors are for example "elongation," "chunkiness," "sphericity," "convexity" and "circularity." Specks and starch particles can be differentiated for example because the circularity (roundness) of the speck deviates more strongly from the value of a sphere.

Color and/or color component can be determined by way of example by a color sensor, in particular by a color image sensor. A system and a method for milling-product characterization with a color image sensor are described for example in the international patent application PCT/EP2009/055877. Such a color image sensor can make possible the use of color information for characterizing the particles in a milled-product stream, by imaging the particles, using the electromagnetic radiation they emit, onto a color image sensor which then captures the electromagnetic radiation on its sensor pixels in a spectrally selective fashion. The color image sensor is preferably a CCD sensor with which the method for measuring the velocity of the particles described below can be implemented.

In particular, a combination of reflected-light illumination and transmitted-light illumination can be used. This makes it possible with the reflected-light illumination to achieve the color information and with the transmitted-light illumination to achieve a higher contour sharpness as compared to a pure reflected-light illumination, in particular also for fast particles (e.g. with diameters of about 200 µm and velocities of about 20 m/s). Such combinations of reflected-light and transmitted-light illumination are described for example in PCT/EP2009/055877.

In particular, one or more of these properties (form, the form factor, the color, a color component and/or the velocity) can be determined by way of real-time evaluation.

Optionally, the properties of the portion of the particles obtained in step c) can be calibrated after step c), that is to say data can be prepared and the properties be compared to the respective process knowhow. In such a calibration, the particle-size distributions, which have been determined separately at first by the laser diffraction and contour processing, are combined to form one common distribution over the entire measurement region. According to a first procedure, the overlap region of the measurement data generated with the two measurement methods can be used to normalize the two particle-size distributions and to combine them. According to a second procedure, the total surface area coverage of the measurement data generated with both measurement methods can be measured and be used together with the respective measurement volume for normalizing the distributions.

The result of both procedures is a projection-surface-area-based distribution which deviates from the more technically relevant mass distribution. "Process knowhow" can be used here to define an appropriate conversion. Bran, for example, tends to be more disk-shaped and flour particles more spherical. When converting surface into mass distribution, this can be taken into account by differentiating between flour and bran for example on the basis of color or form factors and weighting them differently.

It is furthermore conceivable to take into account the influence of milling equipment on the form of the bran. The fluting and especially the milling nip of the milling equipment determine for example the average height of the more disk-shaped bran.

The method can be used for the purposes of optimization, closed-loop control, in particular online closed-loop control, modeling, simulation, monitoring, in particular online monitoring, error detection, error diagnosis, quality control and/or traceability of a machine, a machine combination, a process and/or a plant. Such methods are described for example in the international patent application PCT/EP2009/058351.

As another option, in particular measurement data captured by at least one measurement apparatus, in particular measurement data determined by at least one optical measurement apparatus, can be archived. Characteristic values, rules and conclusions relating to the operation and/or configuration of individual or a plurality of machines and/or plants and/or processes can be derived from the archived measurement data. By way of example, the behavior of an overall mill cannot be described completely by the numerous and complex interactions of the individual machines. In order to still enable closed-loop control of an overall plant, a self-learning and/or experience-based closed-loop control can be used. To this end, the measurement signals of the sensors can for example be linked to a desired or undesired state of the overall mill and be archived in a database. It is possible for a closed-loop algorithm to be based on such a database, which closed-loop algorithm deliberately avoids undesired mill states. Such plants with local and/or global closed-loop control systems are described for example in the international application PCT/EP2009/058351.

In addition, raw measurement data of the measurement apparatuses and/or data prepared from this raw measurement data can optionally be used as experience values in adaptive systems, such as neural networks, in particular for providing open-loop and/or closed-loop control for machines and/or plants and/or processes. For example, a neural network could employ the above-described archived measurement data.

This measurement data could also be employed using what is referred to as "fuzzy control." Measurement data could be archived as processed data (for example a particle-mass distribution derived from the two measurement methods) or in a less processed state (e.g. two separate surface distributions).

As another option, raw measurement data of the measurement apparatuses or measurement data of the measurement apparatuses which has not been processed completely to particle-size distributions, in particular a laser diffraction spectrum averaged over a plurality of individual measurements, can be used directly for closed-loop control.

On the basis of a diffraction image recorded with the method, it is possible to calculate for example by circular integration around the image center a laser diffraction spectrum. This indicates what quantity of light was diffracted how far. For a constant particle-size distribution, this diffraction spectrum or its average value averaged over a sufficient number of individual measurements is also constant. Too strong a grinding results in finer particles and hence in stronger laser diffraction, that is to say more light energy with greater radii. Too little grinding, on the other hand, results in less laser diffraction. The laser diffraction spectrum can thus be used directly for closed-loop control (e.g. the width of a milling nip between two rollers), without reconstructing the actual particle-size distribution. The last step requires a lot of computing time and can cause mathematical errors or inaccuracies which adversely affect the closed-loop control. Closed-loop control on the basis of the laser diffraction spectrum can avoid this problem.

In some embodiments, at least one process parameter of the production method is subjected to open-loop and/or closed-loop control on the basis of the property determined in step c), in particular on the basis of the size distribution of the portion of the particles. In particular, the at least one process parameter can be subjected to open-loop and/or closed-loop control such that it causes the size distribution of the particles to be changed. It is thus possible to regulate an actual size distribution toward a predetermined setpoint size distribution.

In particular in the case of a size-reduction method, i.e. for example a milling method, at least one process parameter can be a width of at least one milling nip, a rotational speed of at least one milling body, a rotational-speed ratio between two milling bodies, a geometry of a milling body and/or a milling roller and/or a mass throughput of a product to be milled. The geometry of a milling roller can for example include its fluting.

In one development of the method, it is possible for velocity measurements of individual particles or for velocity measurements which are locally averaged over the entirety or partial regions of a measurement region for particle-size classes to be used for correcting the particle-size distributions on the basis of different probabilities of occurrence of particles or particle-size classes in the measurement region of the measurement apparatus. As a result, the measurement accuracy and the reliability can be increased with respect to known methods.

In two-phase streams with wide particle-size distributions, particle velocities generally correlate with particle size, particle form and specific weight. In an accelerated stream, for example larger particles have lower velocities than smaller particles, owing to their usually higher mass. The particle velocity can determine the residence time of the particles in the measurement region and thus directly determine the probability of detecting the particle. In order to take this into account, the optically determined particle-size distribution can be corrected in this respect. The relative or absolute velocities can in this case be determined for the individual particles or be determined at least averaged for each relevant particle-size class. The weighting of each particle-size class is then obtained as a function of the particle velocity and the particle size (e.g. projection surface area, diameter or estimated volume). Determination of object velocities in combination with particle-contour recognition per se is state of the art. As a result the velocity distribution of large particles can be measured directly. The fine portion of the size distribution, measured by diffraction, in particular by laser diffraction, has a nearly constant velocity owing to the smaller particle dimensions and masses. The velocity can be determined by extrapolation from the velocity measurement with particle-contour processing.

Optically captured objects with zero velocities are for example optical errors or scratches on the viewing windows or positionally fixed or slowly migrating soiling (with velocities of substantially less than 1 m/s) such as adhering particles or particle content, for example proteins or fats in the case of cereal products. These are not part of the sought particle-size distribution. With a velocity correction, such as described above, they can be weighted automatically with 0 and therefore the results of the particle-size distribution are not distorted.

In the particle-contour processing, stationary or migrating objects can alternatively be filtered out of the measurement data using a separate algorithm. To this end, for example the magnitude difference of two images determined by the sensor, preferably of two directly successive images, can be evaluated instead of a simple image. As a result, stationary defects or nearly stationary soiled areas are automatically canceled out and are no longer visible in the difference image. Alternatively, cumulative particles with approximately constant size and position can be identified as defects and discarded. To this end, a dynamic list with relevant pixels and objects can preferably be established for filtering the measurement results.

Alternatively, and also suitable for the laser diffraction, it is possible, by briefly interrupting the product stream (for example by stopping a sampling screw), for the background without product stream to be re-learned at regular intervals and be used for the continuously adapted correction of the raw data.

The product stream can selectively be periodically switched off for learning a current background for correcting laser diffraction spectra.

The invention furthermore relates to a device for determining a size distribution of particles, in particular for carrying out the above-described method according to the invention.

The device comprises
- a production device for producing a particle-containing product stream using a production method and/or a preparation device for preparing a particle-containing product stream which was produced using a production method,
- at least two measurement apparatuses for capturing at least a portion of the particles and
- a computational unit for determining at least one property of the portion of the particles on the basis of the measurement data determined by the optical measurement apparatuses.

The production method is selected from the group consisting of size-reduction, purifying, separation, mixing and agglomeration methods. At least two of the measurement apparatuses are configured as two different optical measurement apparatuses for optically capturing the portion of the particles. At least one property of the portion of the particles, determined by computational means, is the size distribution of the portion of the particles.

According to the invention, at least one optical measurement apparatus is configured for capturing a diffraction pattern of the particles. Owing to this configuration, this device can be used to achieve the advantages which were already described above in connection with the method according to the invention.

The device can have sampling means for taking a sample from the product stream. Alternatively or additionally, the device can have transport means for transporting the sample to a measurement region. In this case, the measurement apparatuses are configured and arranged such that the sample can be optically captured in the measurement region by means of the measurement apparatuses.

The sampling means can be configured as a sampling screw. Using such a sampling screw, the sample can be taken from a product stream, for example a bulk-material stream. The sample can be taken locally and preferably locally and temporally combined. In local sampling, only product from a portion of the product stream is taken. This can be realized by a sampling screw inserted into the pipe, wherein only product that falls onto the sampling screw is taken. The sampling screw can in this case be configured to be positionally fixed or preferably pivotable.

Temporal sampling means that the entire product is not taken continuously but only for a short time. This process is repeated. If the process runs continuously and with sufficient stability, the patterns removed are sufficiently representative also for time points before and after the sampling.

A sampler which is preferred according to the present invention for taking a sample from the product stream contains a screw casing, which is arranged or arrangeable at least partially in a flow duct in which the product stream flows. The flow duct can be, for example, a downpipe. Furthermore the sampler comprises a sampling screw, which is housed at least partially in the screw casing. The sampling screw serves for removing the sample.

The screw casing and/or the sampling screw can selectively be brought into a receiving position or into a ready position. In the receiving position, particles contained in the product stream can here be received in the screw casing and thus be removed from the product stream using the sampling screw. In the ready position, by contrast, no particles contained in the product stream can be received in the screw casing. Thus, by selecting the receiving position or the ready position, it is possible to set whether particles are removable by the sampling screw or not. In particular, the sampling screw can also continue to rotate in the ready position, without further particles being able to pass into the screw casing. The sampling screw therefore does not need to be stopped between successive samplings.

In some embodiments, the sampling screw and the screw casing can be mounted to be moveable, in particular pivotable, and be arrangeable in a ready position outside the product stream. In this ready position, the sampling screw can convey product that is already present, but no longer receives product. In order to take a sample, the sampling screw and screw casing can then be pivoted into the product stream until the screw is filled. A closing sleeve is not necessary in this embodiment.

The sampler preferably comprises closing means, with which the screw casing and/or the sampling screw can selectively be brought into a receiving position or into a ready position. In the receiving position, the closing means can open the screw casing, such that a receiving position is brought about. In the ready position, the closing means can close the screw casing, such that a ready position is brought about.

The screw casing is preferably configured to be substantially trough-shaped, and the closing means are preferably configured as a closing sleeve. It is furthermore preferable for the closing sleeve to be rotatable, relative to the screw casing, about an axis which is parallel to the rotational axis of the sampling screw or coincides therewith. It is then possible by setting the relative angle between the closing sleeve and the screw casing to selectively set the receiving position or the ready position. This design is particularly simple.

Alternatively, moveable guide plates, pipe diverters or the like can also be used for selectively setting the receiving position and the ready position.

The device can further contain means for singulating and/or dispersing the sample. As a result, representative sampling even at great sample separation and constant forced transport of the product are ensured. This can be advantageous when one of the measurement apparatuses can analyze only a fraction (for example $1/10$ to $1/10\,000$) of the entire product stream. It is possible by way of sample separation to reduce the product amount accordingly.

Furthermore possible are a plurality of product sampling sites, where the sample can be taken. The use of the device can also permit switching between different product sampling sites, for example for providing closed-loop control for the roller parallelism in a roller mill.

Preferably at least one optical measurement apparatus is configured for capturing projection surface areas of the particles.

Likewise preferred are at least two of the measurement apparatuses, in particular an optical measurement apparatus for capturing a diffraction pattern of the particles and another optical measurement apparatus, which are arranged spatially close together. This permits not only the measurement to be carried out in two spatially close optical measurement regions or even in the same optical measurement region, but also allows for a compact construction to be achieved. The at least two measurement apparatuses can preferably be accommodated in a common housing.

In some developments, the device has at least one open-loop circuit and/or closed-loop circuit, with which at least one process parameter of the production device can be subjected to open-loop and/or closed-loop control on the basis of the property determined by the computational unit, in particular on the basis of the size distribution of the portion of the particles.

Preferably the particle surface area coverage (that is to say the average ratio of particle surface area to measurement surface area in the measurement region) in the measurement region is kept substantially constant in order to avoid possible influences on the measurement result. This can be achieved for example as follows: the projection surface areas of all particles (i.e. the particle surfaces) are measured in each image and are thus known. They are averaged over a number of images. The measurement surface area (i.e. the image size) is fixed and likewise known. The device calculates therefrom the respective particle surface area coverage and can make the latter available to a closed-loop control means as an actual value (e.g. as an analog value). The metering unit (e.g. the screw) can increase or decrease the conveyed quantity depending on the deviation from the actual value. This can be achieved by adapting the screw's rotational speed or by changing its filling level. The filling level in turn can, via the cycle of the temporal sample separation, be subjected directly to open-loop and/or closed-loop control.

Preferably the ratio is kept constant in the range of 0.2% to 5%. To this end, the actual value and the setpoint value of the particle surface area coverage can be used as input variables for providing closed-loop control of the temporal sample separation.

Figure 4A:
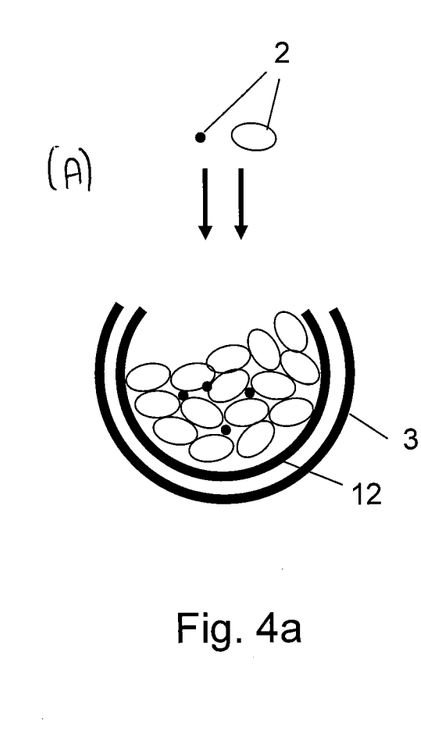
FIGS. 4a and 4b show a sampler of the device according to FIG. 1 with a sampler and a closing sleeve (a) in a receiving position and (b) in a ready position.
Figure 4B:
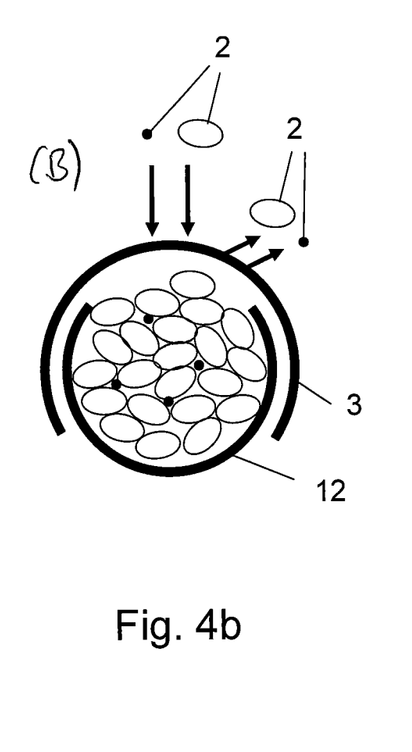

In order to avoid overflow of the product from the screw casing 12 and thus product demixing even in the case of small screw discharge, it is possible according to FIGS. 4a and 4b for the opening of the screw casing 12 to be opened only for a short time for example by way of a rotatable closing sleeve 3 using open-loop or closed-loop control (FIG. 4a), so that a receiving position (A) is achieved, and closed again (FIG. 4b). The closing sleeve is rotatable here about an axis which is parallel to the rotational axis of the sampling screw 5. In the ready position (B) according to FIG. 4b, particles 2 cannot enter the region between screw casing 12 and closing sleeve 3. The closing sleeve 3 can be actuated using a drive (not illustrated here). Alternatively, moveable guide plates, pipe diverters etc. can also be used to open and close the opening of the screw casing 12.

The color sensor can be configured as a color image sensor. A system and a method for milling product characterization with a color image sensor are described for example in the international patent application PCT/EP2009/055877. Such a color image sensor can permit the use of color information for the characterization of the particles in a milling product stream by imaging the particles, using the electromagnetic radiation they emit, onto a color image sensor which then spectrally selectively captures the electromagnetic radiation on its sensor pixels.

At least one of the optical measurement apparatuses can be provided with a viewing window, through which the particles in a measurement region can be captured.

The cleanness of the viewing window is crucial to the quality of the measurement. In order to minimize particles adhering to the viewing windows, the pane material and/or the pane surface structure are preferably chosen such that the physical and/or chemical adhesion forces such as Van der Waals forces, hydrogen bridges, dipole forces and/or liquid bridges for example are as low as possible.

The viewing window can preferably contain or be composed of electrically conductive glasses or transparent plastics. As a result, electrostatic particle adhesion can be largely reduced or even completely avoided. To this end, electrically conductively coated viewing windows can preferably be used. Here, a glass or a plastic can be coated on the inside of a channel in which the portion of the particles is guided. The coating can contain or be composed of for example a film made of indium tin oxide, silicon oxide-based materials or $TiO_2$ (preferably substoichiometric in O).

Accordingly, the invention furthermore relates to the use of a transparent, at least partially electrically conductive material, in particular a transparent material which is provided with an electrically conductive coating, as a viewing window for reducing electrostatic particle adhesion to the viewing window. In particular, the use may be the use as a viewing window in an optical measurement apparatus. The transparent material can contain or be composed of for example a glass or a transparent plastic.

In addition, heating, cooling or alternate heating and cooling can change material properties of the adhering particles and thus minimize the soiling. By vibrating the viewing window or windows, for example using a piezo element, it is additionally or alternatively possible to overcome particle adhesion forces and to thus achieve better cleanness of the viewing window.

Alternatively or additionally it is possible in the method according to the invention to set the particle velocity for different products such that the degree of soiling on the viewing window is as low as possible. Greater velocities reduce the fluid-mechanical boundary-layer thickness at the channel internal sides of the viewing windows and thus result in higher shear forces and higher-energy collisions between moving and adhering particles. With increasing flow velocity, this results in an increasing self-cleaning effect. For finer products such as for example flour and average flow velocities of more than 10 m/s in combination with electrically conductively coated viewing windows, the self-cleaning effect dominates and results in sufficiently clean viewing windows.

For coarser particles such as for example whole-grain cereal, however, high particle velocities can be disadvantageous, because as a result of the higher inertia forces, more solid material deposits on the viewing window can occur when a particle impacts the viewing window as compared to finer particles. This effect occurs in cereal products in particular in the case of fat-rich and/or protein-rich particle surfaces and diminishes the optical properties of the viewing windows. In addition, the higher inertia forces expedite the wear of the components and viewing windows. These negative influences can outweigh the advantageous self-cleaning effect at higher velocities, with the result that in some embodiments of the method lower velocities are preferred, in particular velocities of less than 20 m/s, preferably less than 15 m/s, particularly preferably less than 10 m/s.

Alternatively or additionally it is also possible, owing to the geometric nature of the channel, in which the portion of the particles is guided, for the product guidance to be set such that the particles do not come into contact with, or only rarely come into contact with, the viewing windows and thus particle adhesion is avoided. To this end, it is possible for example to produce a particle-free boundary layer and minimization of the turbulence in the boundary layer by a sudden channel widening with flushing air. In this case, the flushing air can be blown in above and/or below a step in order to shield the viewing windows with cleaner (i.e. particle-free) flushing air and in order to avoid recirculation.

Alternatively or additionally it is possible for a particle-free boundary layer to be produced by a continuous channel widening with porous side walls and homogeneous addition of air through the porous walls.

Likewise alternatively or additionally it is possible in the optical measurement apparatus for capturing a diffraction pattern for a hole to be arranged, which can correspond in particular to the diameter of the laser beam. The viewing window can in this case be recessed. An in particular annular flushing-air gap can be arranged in the region of the viewing window in order to prevent adhesion of the particles to the viewing windows.

The signal of the measurement apparatuses can be used to optimize the product quality and/or to keep it constant. To this end, the measurement apparatus can be used in combination with one or more size-reduction units, such as for example a mill, for example a roller mill, pinned disk mill, impact mill or hammer mill. The milling effect of a roller mill can be adapted for example by way of size and parallelism of the nip between the roller pair, the roller rotational speed or the roller rotational-speed ratio during operation such that the particle-size distribution and/or other particle properties correspond to previously defined setpoint values. In order to check the roller parallelism it is possible with a moveable or at least two positionally fixed sampling locations to divert one or more partial streams at different roller positions and to evaluate these parallel with a plurality of measurement systems or preferably sequentially with one measurement system.

It is possible using the measurement apparatuses to monitor, and subject to open-loop and/or closed-loop control, optical, mechanical and/or aerodynamic cleaning or separation processes, such as for example sifting. A desired particle-size distribution can in this case be achieved by setting machine parameters such as velocity, rotational speed, pressure, volume flow, machine geometry and geometry of the separation devices.

Alternatively or additionally it is possible for the device or the method to be used in order to determine properties of the starting products and/or of the end product during mixing processes or to suitably subject a mixing process to open-loop and/or closed-loop control. In cereal mills, for example, it is possible in this manner to achieve specified end product qualities of flour, semolina, in particular durum semolina or corn semolina, or bran in a more accurate manner. It is furthermore possible with the aid of the method according to the invention and/or the device according to the invention in mixing processes for the mixing ratios and/or machine parameters to be monitored and subjected to open-loop and/or closed-loop control.

In agglomeration processes, such as for example during pelletizing and/or pressure agglomeration, during agglomeration in fluidized layers and/or by flocculation, it is possible for the device according to the invention or the method according to the invention to be used to achieve the desired average agglomerate size or agglomerate-size distribution and/or other agglomerate properties. To this end, during operation, it is possible for, inter alia, the product residence time, process conditions such as temperature, humidity, flow velocities and/or further machine or process parameters to be subjected to open-loop control, closed-loop control and/or be optimized.

By using a color sensor during contour capturing, it is possible to capture, in addition to the particle size, the average color or color components of partial regions of the particle. Preferably, the particle form and/or form factors are determined additionally to the color. The color information can be used to draw conclusions about the material composition of the particles. In the case of cereal grains, it is thus possible to identify for example foreign grains, broken grains, contaminants such as sand and stones or grains infested with parasites or pathogens. In cereal intermediate and end products, it is possible for different grain constituents of the particles to be differentiated. In the case of wheat it is possible with the aid of the color information for the whitish endosperm, the brownish bran and the more yellowish germ to be differentiated. It is also possible for particles to be identified as mixed portions, wherein the method can be used to capture and describe the individual partial regions of a particle in terms of proportion. This procedure is expedient particularly for processes in which grinding, which is selective with respect to the contents, and subsequent separation of the contents are necessary. Other advantages which result from the use of a color image sensor are described in the international patent application PCT/EP2009/055877.

In plants or processes with at least two control variables, it is possible for one or more measurement apparatuses to be used in combination with a data storage means to at least partially describe operating conditions of a plant or a process and to define these conditions for example as good or bad. This produces experience values, which make possible an adaptive system for monitoring, open-loop or closed-loop control of a plant or of a process. Preferably, condition regions of the plants or processes are described mathematically and interpolated and subjected to closed-loop control and/or optimized on the basis of the measurement values.

In order to optimize processes with closed-loop systems, it is also possible for a more comprehensive detection of particle properties and/or machine conditions and/or plant conditions to be achieved by combining the measurement system with further measurement apparatuses, such as for example by supplementing with inductive, capacitive, ultrasound, near-infrared or color sensors.

The device can be used for closed-loop control of processes, in which actual value and setpoint value are available to the closed-loop control as raw data of the laser diffraction or as laser diffraction spectrum and therefore particle-size distributions do not necessarily have to be reconstructed from the raw data of the laser diffraction. The method reduces the computational outlay and optimizes the signal-to-noise behavior of the measurement system.

It is possible to provide closed-loop control for fine product, for example for flours with fine particles, in which directly in the diffraction spectrum rather than a closed-loop control with respect to particle mass or projection surface area. This method is preferably used if at least the majority of the particles falls into the measurement region of the laser diffraction. This is the case only for fine products (for example with a maximum size of 300 μm). This method can be used for flour (typically with sizes of less than 150 μm).

The invention will be described below in an exemplary embodiment with reference to drawings, in which.

Figure 1:
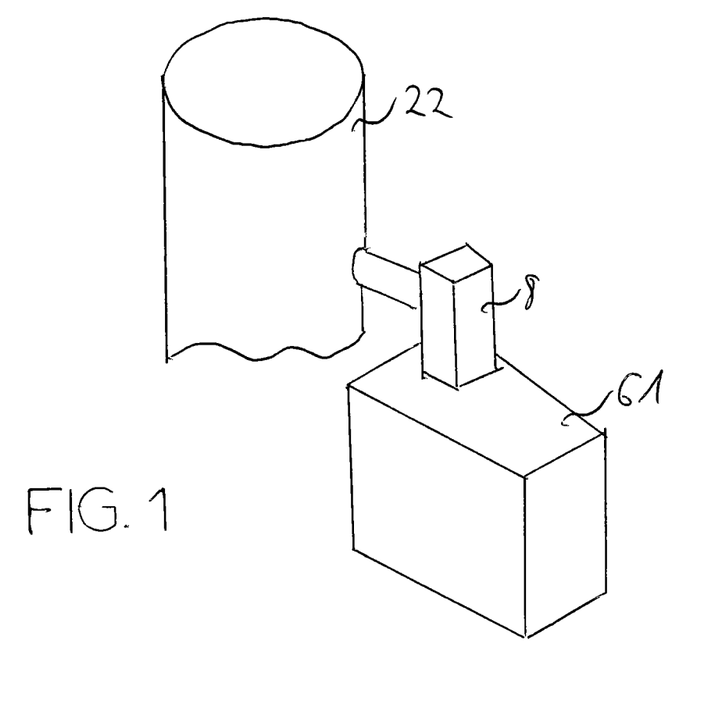
FIG. 1 shows a perspective view of a device according to the invention.

According to FIG. 1, a particle stream is guided vertically downward in a downpipe 22. The particle stream contains particles, as can occur in a grinding process, for example after a size-reduction, cleaning or separation process in a cereal mill. Using sampling means, which are configured as sampler 1, a partial stream of the particles is removed at a measurement location and fed horizontally to a singulator and disperser 8. Sampling is explained in more detail below in connection with FIG. 2. The singulator and disperser 8 is known per se. It can be configured, for example, as a baffle plate (such as described in WO 2006/000112), blower or vibrator or contain throwing blades.

Figure 2:
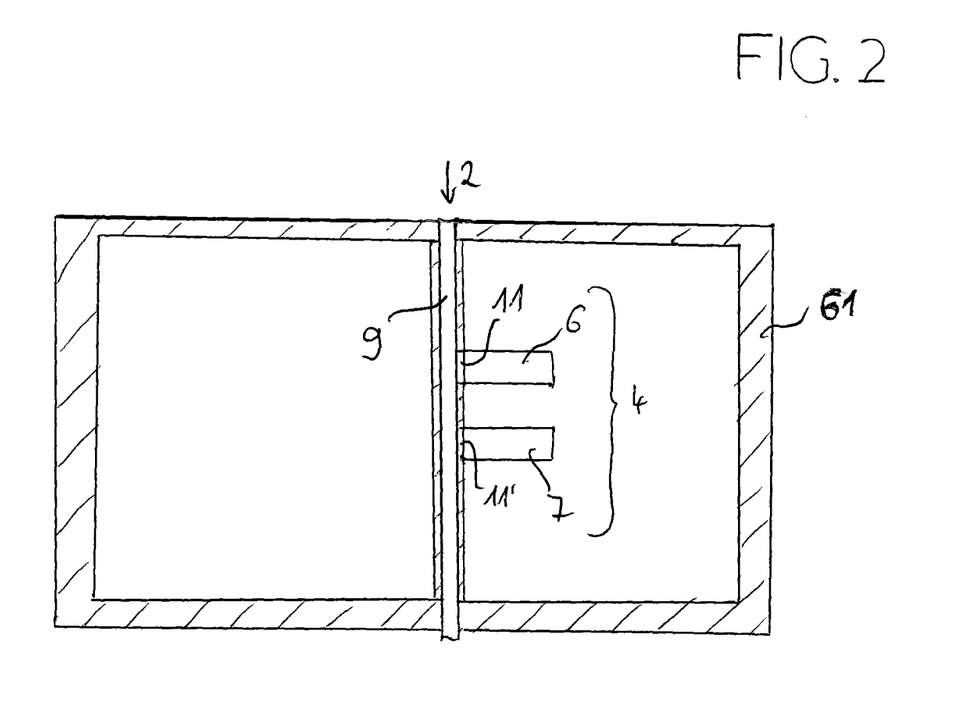
FIG. 2 shows a side sectional view of measurement equipment of the device according to FIG. 1 containing two optical sensors.

According to FIG. 2, the air stream 10 with the entrained particles is then calmed in a channel 9 and presented to two optical sensors 6, 7 of optical measurement equipment 4, which are arranged inside a housing 61. The sensors 6, 7 form two different optical measurement apparatuses. Here, the optical sensor 6 is configured to capture a diffraction pattern of the particles, whereas the optical sensor 7 is configured to capture projection surface areas of the particles. In the exemplary embodiment shown, the optical sensor 7 is arranged downstream of the optical sensor 6; this order is not, however, essential to the invention. Two viewing windows 11, 11' of the channel 9 permit measurement of the particles in the air stream 10. The optical axes of the sensors can be arranged at right angles to the flow direction. Furthermore conceivable is also a deviation of up to 15° from the optically perpendicular alignment of one or both sensors in order to avoid reflections. A concrete combination of two sensors which are accommodated in a housing and can be used in this exemplary embodiment is described for example in German patent application DE 102009014080.

Particles which have passed the sensors 6, 7 can be returned to the main stream using an optional product return line.

By combining the measurement data from the two optical sensors 6, 7, it is possible for particle-size distributions with a bandwidth of up to four particle orders of magnitude to be captured, so that the advantages of the laser diffraction for small particles and those of the particle contour capturing for large particles are combined in one housing.

The particle surface area coverage (that is to say the average ratio of particle surface area to measurement surface area in the measurement region) in the measurement region is preferably kept constant in order to avoid possible influences on the measurement result. Preferably the ratio is kept constant in the range of 0.2% to 5%. To this end, the actual value and setpoint value of the particle surface area coverage can be used as input variables for providing closed-loop control of the temporal sample separation.

Figure 3:
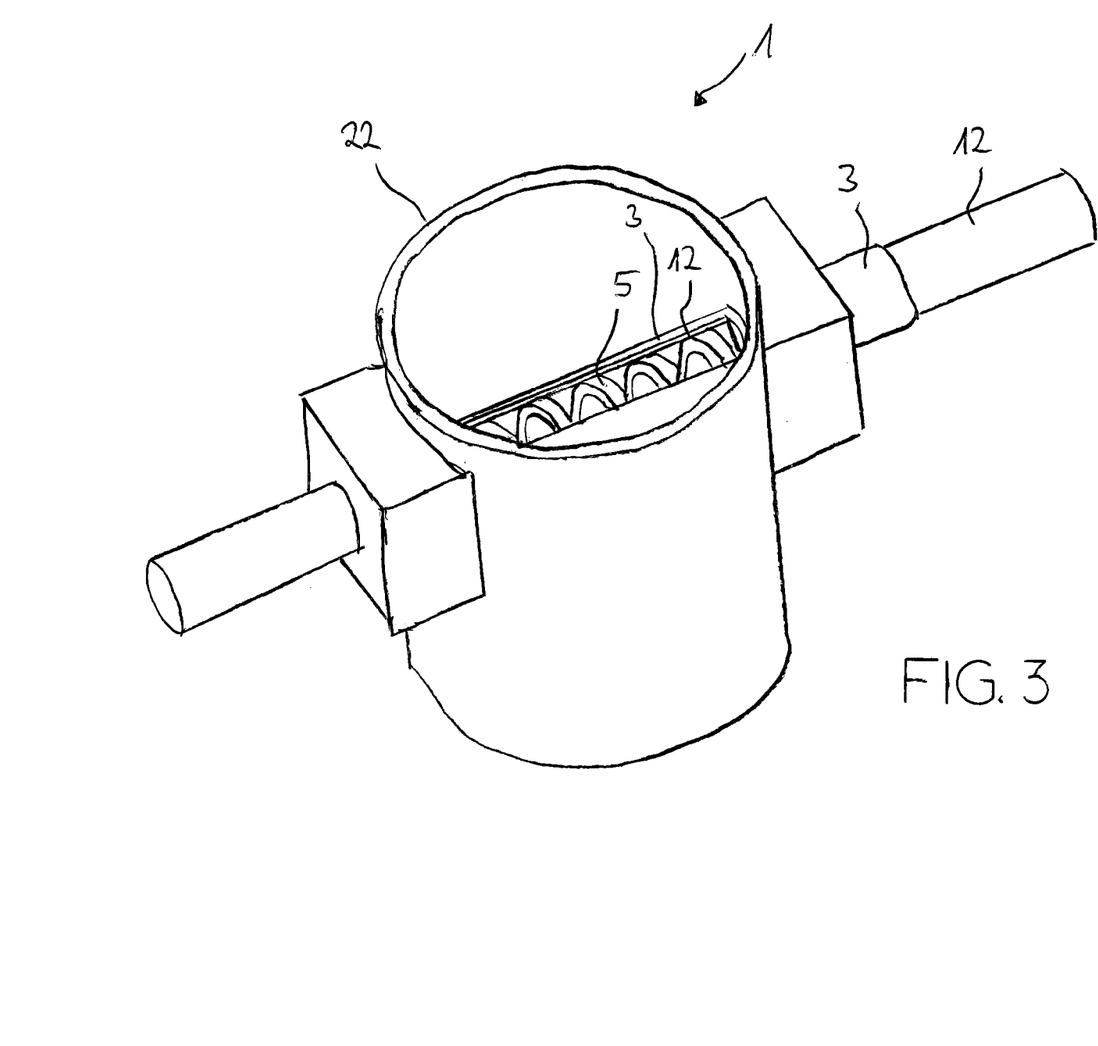
FIG. 3 shows a sampler of the device according to FIGS. 1 and 2.

FIG. 3 shows in detail the sampler 1 for removing a partial stream from the main stream flowing through the downpipe 22. The sampler 1 contains a horizontally arranged sampling screw 5. The underside of the sampling screw 5 is housed in a trough-shaped screw casing 12 (cf. also FIGS. 4a and 4b below). Removal using the sampling screw 5 ensures the representativeness of the sample taken.

In order to avoid overflow of the product from the screw casing 12 and thus product demixing even in the case of small screw discharge, it is possible according to FIGS. 4a and 4b for the opening of the screw casing 12 to be opened only for a short time for example by way of a rotatable closing sleeve 3 using open-loop or closed-loop control (FIG. 4a), so that a receiving position (A) is achieved, and closed again (FIG. 4b). The closing sleeve is rotatable here about an axis which is parallel to the rotational axis of the sampling screw 5. In the ready position (B) according to FIG. 4b, particles 2 cannot enter the region between screw casing 12 and closing sleeve 3. The closing sleeve 3 can be actuated using a drive 31 (not illustrated here). Alternatively, moveable guide plates, pipe diverters etc. can also be used to open and close the opening of the screw casing 12.

Owing to such devices it is possible to remove, in flexible time intervals, a locally sufficiently representative partial stream in the screw casing 12 and feed it, at a constant conveying speed which is small as compared to the main stream, to the measurement equipment 4 with the optical sensors 6, 7. The sampling screw 5 permits the local sample separation, and the closing of the closing sleeve 3 of the sampling screw 5 permits the time distribution. Owing to the intervals of the temporal sample separation, it is additionally possible for the separation ratio of the sampling to be matched flexibly to the process conditions. By combining the sample separation procedures it is possible for a large sample separation ratio of up to 1:10 000 to be made possible. This is not possible for purely local sample separation because here demixing results in non-representative samples. At the same time, the quantities of removed product are smaller than in a purely temporal sample separation and are additionally discharged continuously. As an alternative to closing the screw it may also be possible to pivot the screw out of the product stream. To this end, the sampling screw and screw casing can be mounted such that they can move, in particular pivot, and be arrangeable in a ready position outside the product stream. In this ready position, the sampling screw can convey product which is already present, but does not receive new product. In order to take a sample, the sampling screw and screw casing can then be pivoted into the product stream until the screw is filled. A closing sleeve is not necessary in this configuration. Fluctuations in process mass flows can be compensated for example by way of open-loop or closed-loop control.

Figure 5:
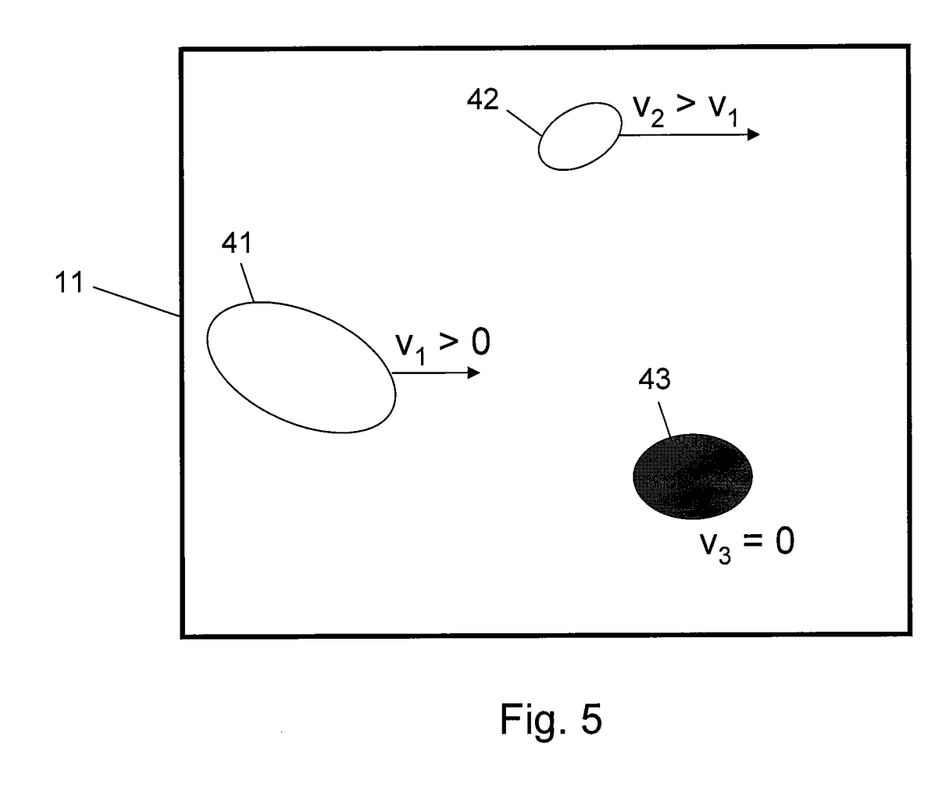
FIG. 5 shows an illustration of the probability of occurrence of a particle.

According to FIG. 5, in an accelerated flow, for example larger particles 41 have, owing to their usually greater mass, lower velocities than smaller particles 42. Since the particle velocity determines the residence time of the particles 41, 42, 43 in the measurement region which is capturable through the viewing window 11 and thus directly determines the probability of detecting the particle, the optically detected particle-size distribution must be corrected with respect thereto. The relative or absolute velocities must in this case be known for the individual particles or be known at least averaged for each relevant particle-size class. The weighting of each particle-size class is then obtained as a function from the particle velocity and the particle size (e.g. projection surface area, diameter or estimated volume). As a result, the velocity distribution of large particles can be measured directly. The fine portion of the distribution, measured by laser diffraction, has a nearly constant velocity owing to the smaller particle dimensions and masses. The latter can be determined by extrapolation from the velocity measurement with particle-contour processing.

Figure 6:
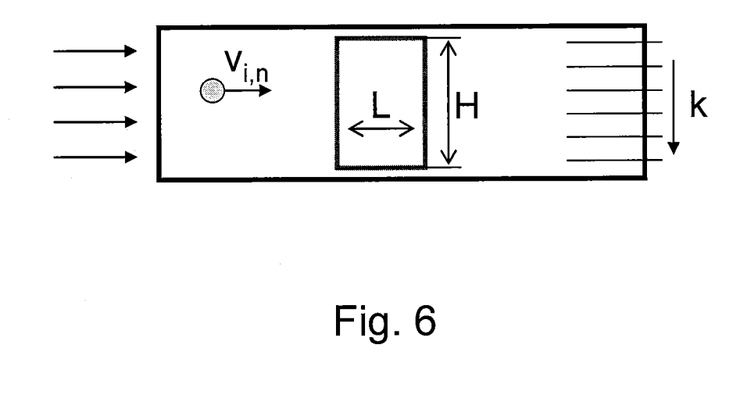
FIG. 6 shows a diagram for explaining a correction of velocity effects.

FIG. 6 shows a diagram of a product channel, which is partially or completely captured by the camera system. The probability of detecting a particle n here depends both on the image height H, the image length B and the image rate f of the optical sensor (which cannot be seen here) and also on particle velocity.

The image velocity $v_B$ is defined as the velocity with which each particle passing through the detection volume in the main flow direction is captured exactly on an image of a measurement series:

$$v_B = f^* L \quad (1)$$

By way of example, for L=15 mm and f=50 Hz, the value $v_B$=0.75 m/s is obtained. Fast particles ($v_{i,n} > v_B$) are measured with a detection probability $P_m$<100%, and this corresponds to a temporal sample separation with:

$$P_m = v_B / v_{i,n} \quad (2)$$

The index i here refers to the particle-size class of the particle n. Slow particles ($v_{i,n} < v_B$) are detected in the statistical mean in $1/P_m > 1$ images. Only the in each case first measurement here improves the particle-size statistic, which is why the particle velocity should be selected to be at least as high as the image velocity.

Equation (2) demonstrates that $P_m$ depends on the individual velocity of the particle n. This must be taken into account when determining the particle mass or surface distribution. Of interest is not primarily the particle-size distribution per image but the mass flow proportions of the individual particle-size classes. Consequently, the product of particle projection surface area or particle mass and velocity forms the basis for the particle-size statistic. Non-moving particles are, for example, detected in each image but make no contribution to the mass flow and are therefore weighted with the velocity zero and ignored in the calculation.

If in any desired number of images overall $n_{tot,i}$ particles of the projection surface area $a_{i,n}$ and velocity $v_{i,n}$ were detected in a particle-size class i, the velocity-corrected overall projection surface area of the particle class i is:

$$a_{tot,i} = \frac{1}{v_B} \sum_{n=1}^{n_{tot,i}} v_{i,n} a_{i,n} \qquad (3)$$

The corrected projection surface area proportion $\alpha_i$ of the particle-size class i is then:

$$\alpha_i = \frac{a_{tot,i}}{\sum_{i=1}^{i_{max}} a_{tot,i}} \qquad (4)$$

In order to be able to also take into account a flow profile transversely to the flow direction and to appropriately correct it, equations 3 and 4 will preferably not be based on the entire channel width but on a width section k (FIG. 6, discretization transversely to the main flow direction). Here, analogously to the consideration hitherto, the following applies:

The cleanness of the viewing window 11 is crucial to the quality of the measurement. In order to minimize particle adhesion to the viewing windows 11, the pane material and/or the pane surface structure are chosen such that the physical and/or chemical adhesion forces such as Van der Waals forces, hydrogen bridges, dipole forces and/or liquid bridges for example are minimal. Electrostatic forces, which are amplified owing to the frequently occurring electrostatic charge in the case of moving bulk materials with wall contact, also have a particular significance. Electrostatic particle adhesion can be largely reduced or even completely avoided by way of viewing windows made of electrically conductive glasses or transparent plastics. To this end, electrically conductively coated viewing windows are preferably used, in which the glass or the plastic is coated on the channel internal side for example with a film made of indium tin oxide. Alternative coatings can be, inter alia, also silicon oxide-based materials or $TiO_2$ (preferably substoichiometric in O). In addition, heating, cooling or alternate heating and cooling can change material properties of the adhering particles and thus minimize the soiling. By vibrating the viewing windows, for example using a piezo element, it is additionally or alternatively possible to overcome particle adhesion forces and to thus achieve better cleanness of the viewing window.

In addition, the particle velocity for different products is also optimized such that the degree of soiling on the viewing window is as low as possible. Greater velocities reduce the fluid-mechanical boundary-layer thickness at the channel internal sides of the viewing windows and thus result in higher shear forces and higher-energy collisions between moving and adhering particles. With increasing flow velocity, this results in an increasing self-cleaning effect. For finer products such as for example flour and average flow velocities of more than 10 m/s in combination with electrically conductively coated viewing windows, the self-cleaning effect dominates and results in sufficiently clean viewing windows.

For coarser particles such as for example whole-grain cereal, however, high particle velocities can be disadvantageous, because as a result of the higher inertia forces, more solid material deposits on the viewing windows can occur when a particle impacts the viewing window as compared to finer product. This effect occurs in cereal products in particular in the case of fat-rich and/or protein-rich particle surfaces and diminishes the optical properties of the viewing windows. In addition, the higher inertia forces expedite the wear of the components and viewing windows. These negative influences can outweigh the advantageous self-cleaning effect at higher velocities, with the result that lower velocities (<15 m/s) are preferred. It is also possible owing to the geometric nature of the flow channel for the product guidance to be optimized such that the particles do not come into contact with, or only rarely come into contact with, the viewing windows and thus particle adhesion is avoided.

Figure 7A:
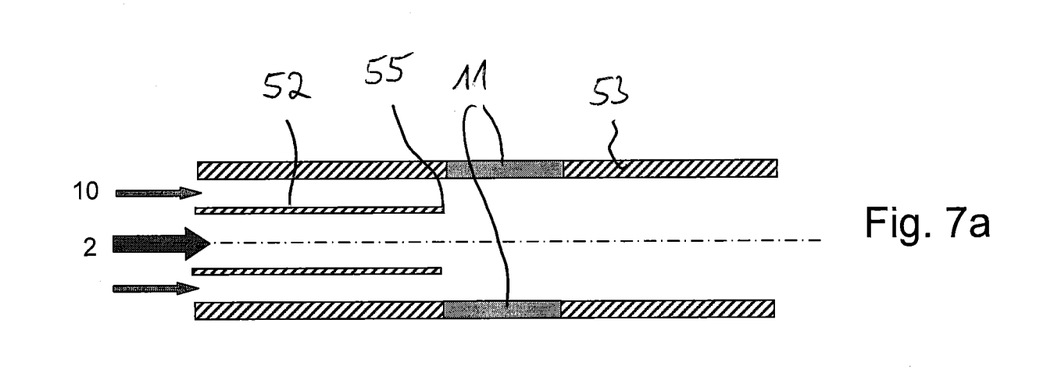
FIGS. 7a and 7b show schematics of means for preventing contact between a product and a viewing window.

To this end, it is possible for example according to FIG. 7a to produce a particle-free boundary layer and minimization of the turbulence in the boundary layer by a sudden widening of a channel with flushing air. To this end, the product stream 2 is guided through an interior channel 52, which ends in the interior space of an exterior channel 53, which is arranged outside, with a greater channel height. The product stream 2 can emerge from the interior channel 52 at this end 55. The wall of the exterior channel 53 contains two viewing windows 11, which are arranged in the region of the end 55 of the interior channel 52. Flushing air 10, which keeps the product stream 2 away from the viewing windows 11 and thus prevents them from being soiled, flows between the interior channel 52 and the exterior channel 53.

Figure 7B:
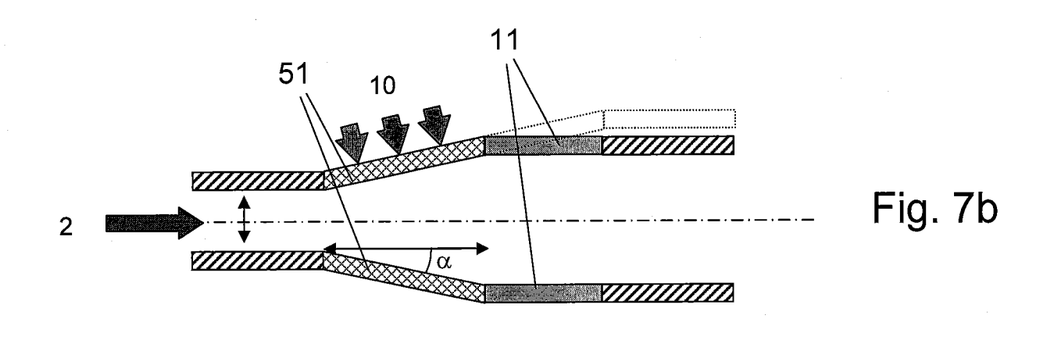

Alternatively, according to FIG. 7b it is possible for a particle-free boundary layer to be produced by a continuous widening of the channel with porous side walls 51 and homogeneous addition of air through the porous side walls 51. The channel is widened in the exemplary embodiment illustrated at an angle $\alpha$ of 18°. However, other angles are of course also feasible, preferably between 6° and 30°.

Figure 8A:
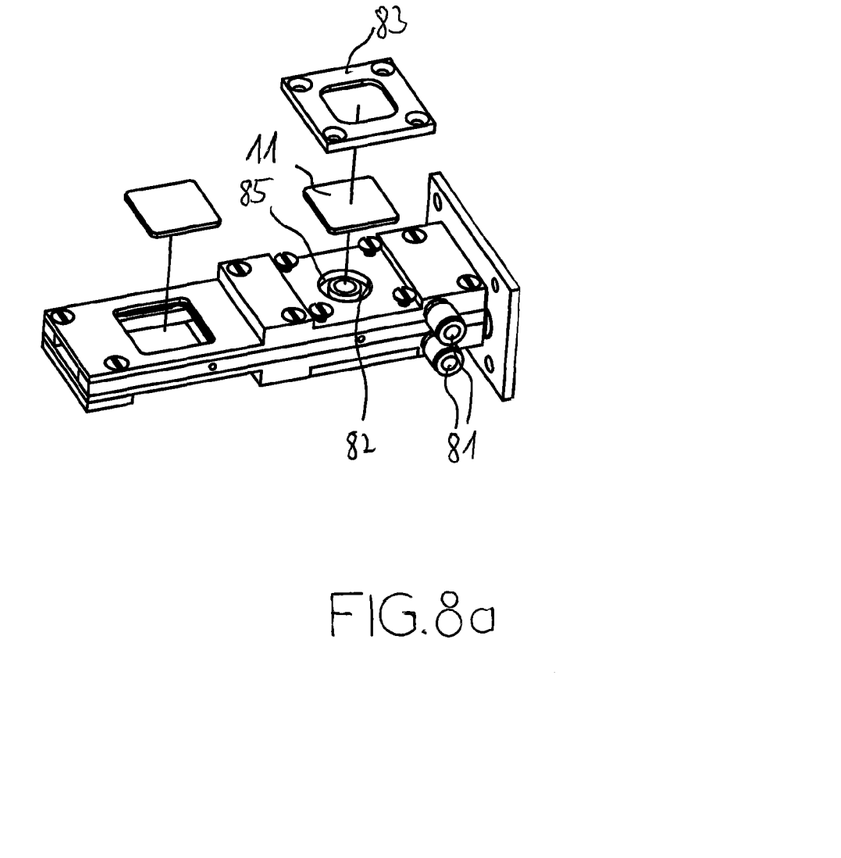
FIGS. 8a and 8b show further means for preventing contact between a product and a viewing window.
Figure 8B:
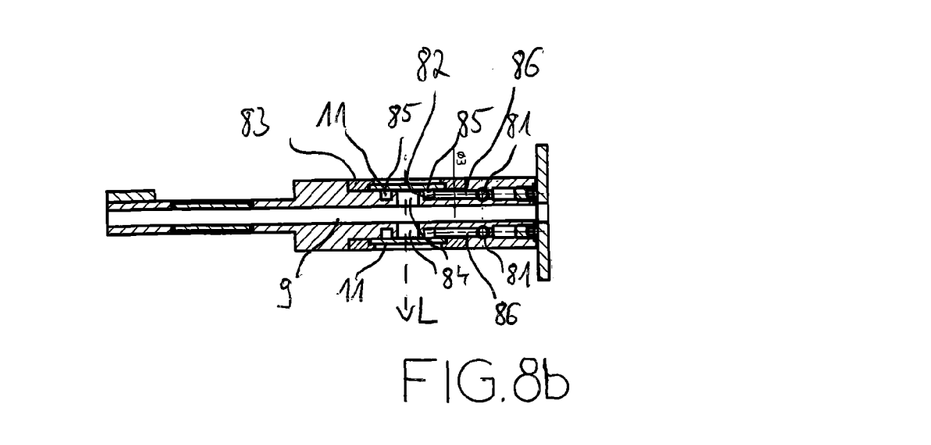

In a further variant, illustrated in FIGS. 8a and 8b, it is possible for a hole to be present, which corresponds to the diameter of a laser beam, with a recessed viewing window 11 and an annular flushing-air gap 85 in the region of the viewing window 11. According to the perspective exploded illustration in FIG. 8a, flushing air is introduced through air inlets 81 into air channels 86 and emerges at air outlets 82 into the annular flushing-air gap 85. From here, the flushing air flows via holes 84 radially into the channel 9 (cf. FIG. 8b). At two opposite sides of the channel 9, in each case a viewing window 11 is arranged, of which FIG. 8a shows only one. This viewing window 11 is fixed using a cover 83.

According to the side sectional view in FIG. 8b, a laser beam L is guided through the two opposite viewing windows 11, the holes 84 and the channel 9 and the product stream guided in said channel. Owing to the flushing air which flows through the air outlets 82 and the holes 84 in the direction of the channel 9, the particles contained in the product stream cannot reach the viewing windows 11, which counteracts any soiling thereof.

The invention claimed is:
1. A method for determining a size distribution of particles, in use in the area of processing of cereal, cereal grinding products and cereal end products of milling or special milling or in the production of feedstuff for farmed or domestic animals, fish and crustaceans, for particles in a particle-containing product stream produced by size-reduction, purifying, separation, mixing and/or agglomeration and having particle sizes ranging from 2 μm to 20 mm, said method comprising the following steps:
   a) generating measurement data by optically capturing at least a portion of the particles using at least two different optical measurement methods at a measurement region, wherein at least one optical measurement method comprising the capturing of a laser diffraction pattern of the portion of the particles and at least one optical measurement method comprises the capturing of projection surface areas of the portion of the particles, b) determining particle size distributions of the portion of the particles on the basis of the measurement data which is captured optically in step a); and c) calibrating the determined particle size distributions, whereby the particle size distributions are combined to form one common distribution over the entire measurement region.

2. The method as claimed in claim 1, wherein a particle-containing sample is taken from the product stream and the particles in the sample are optically captured.

3. The method as claimed in claim 1, wherein at least one additional property of the portion of the particles is determined in step b), comprising at least one property selected from the group consisting of the form, the form factor, the color, a color component and the velocity of the portion of the particles.

4. The method as claimed in claim 1, wherein the particles are produced by size reduction.

5. The method as claimed in claim 1, wherein at least one process parameter of the size reduction, the purifying, the mixing or the agglomeration is subjected to a control selected from the group selected from one of open-loop and closed-loop control on the basis of at least one of the particles size distributions determined in step b or c) or an additional property of the portion of the particles determined in step b) comprising at least one property selected from the group consisting of the form, the form factor, the color, a color component and the velocity of the portion of the particles.

6. A device for determining a size distribution of particles, in use in the area of processing of cereal, cereal grinding products and cereal end products of milling or special milling or in the production of feedstuff for farmed or domestic animals, fish and crustaceans, in use on particles in a particle-containing product stream produced by size-reduction, purifying, separation, mixing and/or agglomeration and having particle sizes ranging from 2 μm to 20 mm, said device comprising at least two different optical measurement apparatuses for optically capturing at least a portion of the particles at a measurement region, wherein at least one optical measurement apparatus is configured for capturing a laser diffraction pattern of the portion of the particles, at least one optical measurement apparatus is configured for capturing projection surface areas of the portion of the particles, a computational unit which determines particle size distributions of the portion of the particles on the basis of the measurement data captured by the optical measurement apparatuses, and calibrates the determined particle size distributions, whereby the particle size distributions are combined to form one common distribution over the entire measurement region.

7. The device as claimed in claim 6, further comprising sampling means for taking a sample from the product stream and transport means for transporting the sample to the measurement region.

8. The device as claimed in claim 6, further comprising a sensor selected from the group consisting of an inductive, capacitive, ultrasound, near-infrared and color sensor.

9. Use of the device as claimed in claim 6, for open-loop or closed-loop control of at least one process parameter of the size reduction, the purifying, the separation, the mixing or the agglomeration on the basis of at least one of the particle size distributions determined by the computational unit or an additionally-determined property of the portion of the particles determined by the computational unit and comprising at least one property selected from the group consisting of the form, the form factor, the color, a color component and the velocity of the portion of the particles.

10. The method as claimed in claim 2, wherein the particle-containing sample is taken with a sampler, the sampler containing a screw casing, which is arranged or arrangeable at least partially in a flow duct, a sampling screw, which is housed at least partially in the screw casing, for taking the sample, wherein at least one element selected from the group consisting of the screw casing and the sampling screw can selectively be brought into a receiving position or into a ready position, wherein, in the receiving position, particles contained in the product stream can be received in the screw casing and, in the ready position, no particles contained in the product stream can be received in the screw casing.

11. The method as claimed in claim 10, wherein the sampler has closing means, with which the screw casing or the sampling screw can selectively be brought into the receiving position or into the ready position.

12. The method as claimed in claim 11, wherein the screw casing is configured to be substantially trough-shaped, the closing means are configured as a closing sleeve, which is rotatable, relative to the screw casing, about an axis which is parallel to the rotational axis of the sampling screw or coincides therewith.

13. The device as claimed in claim 7, wherein the sampling means contain a screw casing, which is arranged or arrangeable at least partially in the flow duct, a sampling screw, which is housed at least partially in the screw casing, for taking the sample, wherein at least one element selected from the group consisting of the screw casing and the sampling screw can selectively be brought into a receiving position or into a ready position, wherein, in the receiving position, particles contained in the product stream can be received in the screw casing and, in the ready position, no particles contained in the product stream can be received in the screw casing.

14. The device as claimed in claim 13, wherein the sampling means has closing means, with which the screw casing or the sampling screw can selectively be brought into the receiving position or into the ready position.

15. The device as claimed in claim 14, wherein the screw casing is configured to be substantially trough-shaped, the closing means are configured as a closing sleeve, which is rotatable, relative to the screw casing, about an axis which is parallel to the rotational axis of the sampling screw or coincides therewith.

16. The method as claimed in claim 1 for determining a size distribution of particles having particle sizes ranging from 5 μm to 5 mm.

17. The method as claimed in claim 1, wherein the sample is metered, singulated and/or dispersed before step a).

18. The method as claimed in claim 1, wherein the particles are entrained in an air stream and optically captured in said airstream.

19. The method as claimed in claim 1, wherein at least the finer particles have an average flow velocity of more than 10 m/s in the region of a viewing window in the measurement region.

20. The device as claimed in claim 6, for determining a size distribution of particles having particle sizes ranging from 5 µm to 5 mm.

21. The device as claimed in claim 6, further comprising means for singulating and/or dispersing the sample.

22. The device as claimed in claim 6, further comprising means for generating an air stream in which the particles are entrainable and optically capturable.

* * * * *